(12) United States Patent
Tanabe et al.

(10) Patent No.: US 7,268,258 B2
(45) Date of Patent: Sep. 11, 2007

(54) PROCESS FOR PRODUCING MUSCONE AND ITS INTERMEDIATE

(75) Inventors: Yoo Tanabe, Sanda (JP); Tomonori Misaki, Sanda (JP); Ryohei Nagase, Sanda (JP); Kunshi Matsumoto, Sanda (JP)

(73) Assignee: Takasago International Corporation, Tokyo (JP)

( * ) Notice: Subject to any disclaimer, the term of this patent is extended or adjusted under 35 U.S.C. 154(b) by 91 days.

(21) Appl. No.: 11/290,808

(22) Filed: Dec. 1, 2005

(65) Prior Publication Data

US 2006/0135819 A1   Jun. 22, 2006

(30) Foreign Application Priority Data

Dec. 1, 2004 (JP) ............................. 2004-348409

(51) Int. Cl.
*C07C 45/45*     (2006.01)
*C07C 69/66*     (2006.01)

(52) U.S. Cl. ......................... 568/354; 560/174
(58) Field of Classification Search .................... None
See application file for complete search history.

(56) References Cited

OTHER PUBLICATIONS

Indo, Motoichi, "Synthetic Perfume, Chemistry and Product Information", The Chemical Daily Co., Ltd., Mar. 3, 1996, pp. 492-497.
"Latest Technologies of Synthetic Perfume", CMC Publishing Co., Ltd., published in 1982, pp. 71-90.
Louie, Janis et al., "Tandem Catalysis: The Sequential Mediation of Olefin Metathesis, Hydrogenation, and Hydrogen Transfer with Single-Component Ru Complexes," *J. Am. Chem. Soc.*, 2001, vol. 123, pp. 11312-11313.
Mathew, Jacob et al., "A Novel Route to Substituted Cyclopent-2-en-1-one; Application to the Synthesis of *cis*-Jasmone and Dihydrojasmone," *J. Chem. Soc., Chem. Commun.*, 1990, pp. 684-686.
Misaki, Tomonori et al., "Tri-*Crossed*-Claisen Condensation between Carboxylic Esters and Acid Chlorides or Acids: A Highly Selective and General Method for the Preparation of Various β-Keto Esters," *J. Am. Chem. Soc.*, 2005, vol. 127, pp. 2854-2855.

Primary Examiner—Sikarl A. Witherspoon
(74) Attorney, Agent, or Firm—Kubovcik & Kubovcik

(57) ABSTRACT

The present invention provides a process for producing a muscone represented by (1) by subjecting a citronellic acid derivative and an undecenoate to a Claisen condensation reaction to produce a keto ester compound represented by (2) decarboxylating the keto ester compound to produce 2,6-dimethyl-8-oxy-2,17-heptadecadiene, cyclizing the heptadecadiene using a metathesis catalyst to produce a 6-dehydromuscone represented by (3) and then hydrogenating the double bond. The present invention also provides the keto ester compound

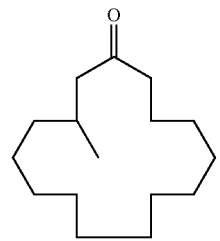
(1)

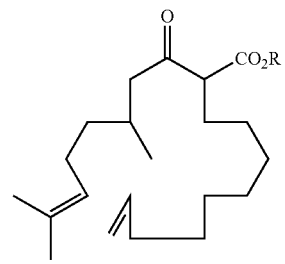

(2)

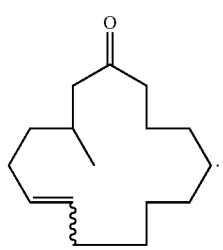

(3)

14 Claims, No Drawings

PROCESS FOR PRODUCING MUSCONE AND ITS INTERMEDIATE

BACKGROUND OF THE INVENTION

1. Field of the Invention

The present invention relates to a process for producing a muscone and an intermediate of the muscone and, more particularly, to a process capable of producing an intended muscone in a short process at a high yield and also relates to a novel intermediate useful for producing the muscone.

2. Description of the Related Art

Recently, the orientation of people toward natural products is increased, and with regard to highly preferred perfumes allowing the imagination specific to nature, it has been strongly desired to develop fragrances derived from natural compounds or fragrances that are the same as or similar to natural compounds in view of safety.

A muscone that is one of such fragrances and is represented by the following formula (6) is a compound that is a major fragrance component of natural musk. It is contained in an amount of 0.5 to 2.0% in natural musk and was discovered by Walbaum in 1906. It has a chemical structure determined by Ruzicka in 1926. A natural muscone is (−)-(R)-3-methylcyclopentadecanone while a commercial product is a synthetic product and a dl-isomer.

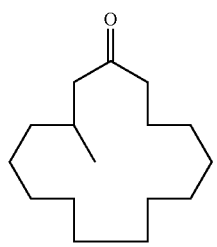

(6)

When the fragrance of a (−)-(R)-isomer of a muscone is compared with that of a (+)-(S)-isomer of a muscone, the (R)-isomer has a diffusive musk fragrance (threshold value: 3 ppm) whereas the (S)-isomer has a chemically non-expansive, poor and weak musk fragrance (threshold value: 10 ppm), with the result that as to the intensity of fragrance, it is known that the (R)-isomer has an intensity of fragrance three times stronger than that of the (S)-isomer (Motoichi Indo, "Synthetic Perfume, Chemistry and Product Information", The Chemical Daily Co., Ltd., published on Mar. 3, 1996, pp. 492-497; and "Latest Technologies of Synthetic Perfume", CMC Publishing Co., Ltd., published in 1982, pp. 72-90).

In view of this situation, many studies have been made as to a method of producing a muscone and particularly, a (−)-(R)-muscone and the results of these studies have been reported. Among these methods, there are some methods that have been reported for producing a (−)-(R)-muscone using optically active citronellal as an asymmetric source. For example, a method has been reported in which (1) a hydroxyl group of a long-chain secondary alcohol synthesized from optically active citronellal and 9-decenyl Grignard reagent is protected with a silyl group, (2) the both-terminal dialdehyde group generated by ozonolysis is converted into a both-terminal diolefin by a methyl Wittig reaction, (3) the silyloxy group is deprotected, (4) the hydroxyl group is converted into a ketone by Jones oxidation, followed by (5) metathesis cyclization and then (6) the double bond is hydrogenated to obtain an optically active muscone (J. Chem. Soc., Perkin., 1, 2253 (1998) which is incorporated herein by reference).

This production method, however, involves using expensive 9-decenyl Grignard reagent, and requires many steps including a step of protecting and deprotecting a hydroxyl group, two oxidizing steps for ozonolysis and Jones oxidation and a Witting reaction step using a butyllithium reagent and, therefore, has the drawback that the process is too long. It must be said that it is difficult to adopt this method for industrial production of a (−)-(R)-muscone.

Also, a method has been reported in which a shorter process is attained wherein a long-chain secondary alcohol synthesized from optically active citronellal and a 9-decenyl Grignard reagent is subjected to metathesis cyclization, the obtained macrocyclic alcohol is subjected to a dehydrogenation reaction to make a corresponding ketone and then the double bond is hydrogenated to obtain an optically active muscone (J. Am. Chem. Soc., 123, 11312 (2001))

However, in this method, it is likewise necessary to use an expensive 9-decenyl Grignard reagent and therefore it cannot be said that this method is satisfactory.

SUMMARY OF THE INVENTION

It is therefore necessary to develop a method capable of producing an intended muscone, particularly, a (−)-(R)-muscone in a shorter process at a higher yield to solve these problems.

The above prior art problem can be solved by the present invention as shown below.

(1) A process for producing a muscone represented by the following formula (6):

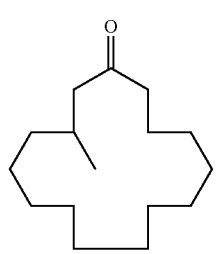

(6)

the process comprising running a Claisen condensation reaction between a citronellic acid derivative represented by the general formula (1):

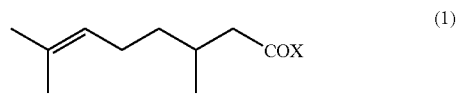

(1)

wherein X represents a hydroxyl group or a halogen atom, and an undecenoate represented by the following general formula (2):

(2)

wherein R represents a lower alkyl group, to produce a keto-ester compound represented by the following general formula (3):

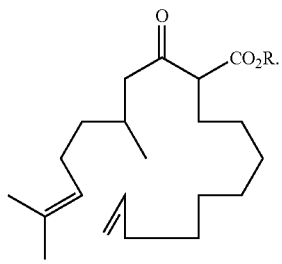
(3)

wherein R has the same meaning as above, then running a decarboxylation reaction of the keto ester compound to produce 2,6-dimethyl-8-oxy-2, 17-heptadecadiene represented by the following formula (4):

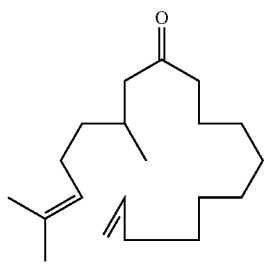
(4)

then running a cyclization reaction using a metathesis catalyst to produce a 6-dehydromuscone represented by the following formula (5)

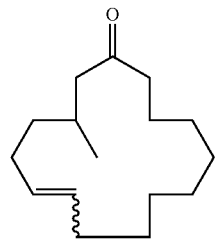
(5)

wherein the wavy line shows that a sixth-position double-bond cis-isomer and/or trans-isomer is contained, and then hydrogenating the double bond.

(2) A process for producing a (R)-muscone represented by the following formula (6-a):

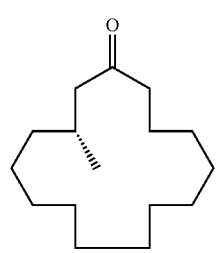
(6-a)

the process comprising running a Claisen condensation reaction between a (R)-citronellic acid derivative represented by the general formula (1-a):

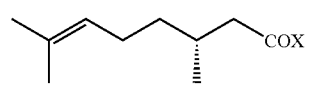
(1-a)

wherein X represents a hydroxyl group or a halogen atom, and an undecenoate represented by the following general formula (2):

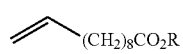
(2)

wherein R represents a lower alkyl group, to produce a (6R)-keto ester compound represented by the following general formula (3-a):

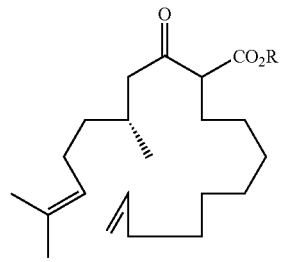
(3-a)

wherein R has the same meaning as above, then running a decarboxylation reaction of the keto ester compound to produce (6R)-2,6-dimethyl-8-oxy-2,17-heptadecadiene represented by the following formula (4-a):

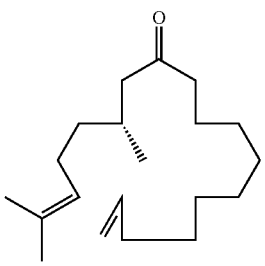
(4-a)

then running a cyclization reaction using a metathesis catalyst to produce a (R)-6-dehydromuscone represented by the following formula (5-a):

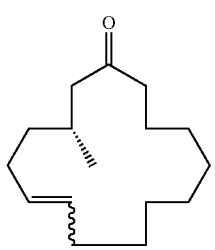
(5-a)

wherein the wavy line shows that a sixth-position double-bond cis-isomer and/or trans-isomer is contained and then hydrogenating the double bond.

(3) A process for producing a keto ester compound represented by the following general formula (3):

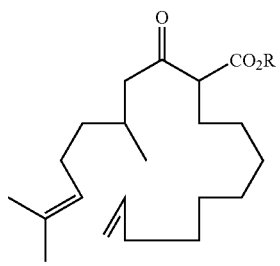

wherein R has the same meaning as above, the process comprising subjecting a citronellic acid derivative represented by the general formula (1):

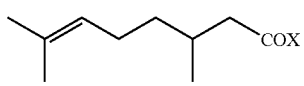

wherein X represents a hydroxyl group or a halogen atom, and an undecenoate represented by the following general formula (2):

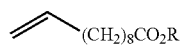

wherein R represents a lower alkyl group, to a Claisen condensation reaction.

(4) A process for producing a (6R)-keto ester compound represented by the following general formula (3-a):

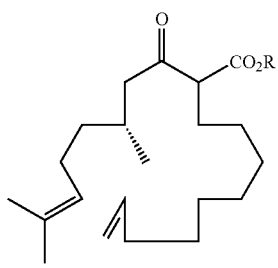

wherein R has the same meaning as above, the process comprising subjecting a (R)-citronellic acid derivative represented by the following general formula (1-a):

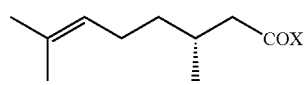

wherein X represents a hydroxyl group or a halogen atom, and an undecenoate represented by the following general formula (2):

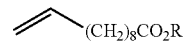

wherein R represents a lower alkyl group, to a Claisen condensation reaction.

(5) A production process according to any one of the above (1) to (4), wherein X in the general formula (1) representing the citronellic acid derivative is a hydroxyl group and the Claisen condensation reaction between citronellic acid derivative represented by the general formula (1) and the undecenoate represented by the general formula (2) is run in the presence of a carboxylic acid activator, a titanium catalyst, a trialkylamine and a N-alkylimidazole.

(6) A production process according to any one of the above (1) to (4), wherein X in the general formula (1) representing the citronellic acid derivative is a halogen atom and the Claisen condensation reaction between the citronellic acid derivative represented by the general formula (1) and an undecenoate represented by the general formula (2) is run in the presence of a titanium catalyst, a trialkylamine and an N-alkylimidazole.

(7) A keto ester compound represented by the following general formula (3):

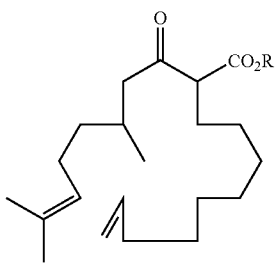

wherein R represents a lower alkyl group.

(8) A (6R)-keto ester compound represented by the following general formula (3-a):

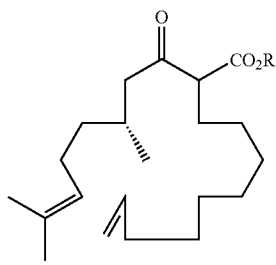

wherein R represents a lower alkyl group.

Specifically, the inventors of the present invention have made earnest studies to solve the above prior art problems, and as a result, have found that a muscone can be produced in a short process at a high yield under practical conditions by first subjecting a citronellic acid derivative and an undecenoate to a Claisen condensation reaction to synthesize a keto ester compound that is a novel compound and is useful for producing a muscone. Next, a decarboxylation reaction is carried out to thereby synthesize 2,6-dimethyl-8-oxy-2,17-heptadecadiene from the keto ester compound. Then the synthesized 2,6-dimethyl-8-oxy-2,17-heptadecadiene is cyclized using a metathesis catalyst and the double bond is hydrogenated. The inventors found further that an optically active muscone can be produced at a high yield by using an optically active citronellic acid derivative as a starting material. The inventors have made further studies to complete the present invention.

In the production process of the present invention, as mentioned above, the process is, unlike the prior art, carried out not through the Wittig reaction in which significant waste is produced. Also, in the production process of the present invention, it is unnecessary to run a reaction at an extremely low temperature and it is also unnecessary to use a dangerous butyl lithium reagent and a strong base which is used in the usual Claisen condensation reaction. Also, the production process of the present invention does not require an oxidation step and does not use an expensive Grignard reagent.

Also, the production process of the present invention comprises a shorter process and can produce a (R)-muscone at a high yield as will be clear in the examples explained later. Therefore, the present invention is very useful for industrial production of a muscone and particularly a (R)-muscone.

DESCRIPTION OF THE PREFERRED EMBODIMENTS

The present invention will be explained in detail below.

In the present invention, first, a citronellic acid derivative represented by the general formula (1) and an undecenoate represented by the general formula (2) are subjected to a Claisen condensation reaction to thereby produce a keto ester compound represented by the general formula (3).

The substituent X in the general formula (1) representing the citronellic acid derivative represents a hydroxyl group or a halogen atom. Both of these citronellic acid derivatives are known compounds and are available as commercial products or the like or may be synthesized from commercial products or the like by a known method.

The substituent R in the general formula (2) representing an undecenoate represents a lower alkyl group, preferably an alkyl group having 1 to 7 carbon atoms and more preferably an alkyl group having 1 to 5 carbon atoms. It is to be noted that this undecenoate is a known compound and is readily available.

When the Claisen condensation reaction between the citronellic acid derivative represented by the general formula (1) and the undecenoate represented by the general formula (2) is run, the molar ratio of the compounds is preferably in a range from 0.5/1 to 1/0.5 and particularly preferably 1/1. Also, the Claisen condensation reaction is run in the presence of a Lewis acid catalyst. Examples of the Lewis acid catalyst include a titanium catalyst and a zirconium catalyst and among these catalysts, a titanium catalyst is preferable. As this titanium catalyst, titanium tetrahalides are preferable and titanium chloride (IV) represented as $TiCl_4$ may be given as a particularly preferable example. Also, the amount of the catalyst may be in a range of 1 to 10 mol equivalents and preferably 2 to 5 mol equivalents to the citronellic acid derivative.

The Claisen condensation is preferably carried out in the presence of an amine. Examples of the amine include trialkylamines having three alkyl groups which may be the same or different. Preferable examples of the amine include tributylamine, diisopropylethylamine and triethylamine. The amount of the amine is designed to be preferably in a range of 0.5 to 2 mol equivalents to the titanium catalyst.

In the Claisen condensation reaction between the above citronellic acid derivatives and undecenoate, a condensation reaction between the two proceeds to obtain a keto ester compound (cross condensation compound) represented by the general formula (3) and also, there is the possibility that a condensation reaction among undecenoates proceeds to produce a keto ester (self condensation compound) as a byproduct. In order to suppress the generation of the byproduct, the Claisen condensation reaction is preferably run in the presence of an N-alkylimidazole represented by the following formula in the present invention.

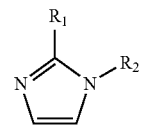

In the formula, the substituents $R_1$ and $R_2$ respectively represent a lower alkyl group and preferably an alkly group having 1 to 5 carbon atoms. The amount of the N-alkylimidazole is preferably almost equivalent to or more than that of the above undercenoate.

The Claisen condensation reaction is run in a solvent including a hydrocarbon type solvent such as toluene or a halogenated hydrocarbon solvent such as dichloromethane or chlorobenzene. There is no particular limitation with respect to the concentrations of the above citronellic acid derivative and undecenoate in the solvent.

When the substituent X in the general formula (1) representing the citronellic acid derivative is a hydroxyl group, it is preferable to use a carboxylic acid activator in addition to the above titanium catalyst. Examples of this carboxylic acid activator may include halogenomethyl carbonate, halogenoethyl carbonate, halogenopropyl carbonate, halogeno-t-butyl carbonate, trihalogenoacetyl halide, isobutanol halide and pivaloyl halide. The amount of activator is 1.0 to 2.0 equivalents and preferably 1.5 equivalents to the above citronellic acid derivative.

Also, when this carboxylic acid activator is used, a base is preferably used with the intention of trapping the acids to be produced. Examples of the base may include inorganic bases such as lithium hydride, sodium hydride, potassium hydride and t-butylpotassium and tertiary amines such as triethylamine, tributylamine and diisopropylethylamine. The amount of the base is 0.8 to 1.2 equivalents and preferably about 1.0 equivalent to the above carboxylic acid activator.

The Claisen condensation reaction proceeds rapidly when the reaction temperature is controlled appropriately, making it possible to obtain an intended keto ester compound represented by the general formula (3).

The structure of the obtained keto ester compound can be confirmed by a nuclear magnetic resonance absorption spectroscopy, an infrared absorption spectroscopy or a high resolution mass spectroscopy. This keto ester compound is an important intermediate in the production of a muscone according to the present invention and is also a novel compound as will be explained later. Also, there has been no report as to the Claisen condensation reaction between the above citronellic acid derivative and undecenoate.

On the other hand, when (R)-citronellic acid derivative represented by the formula (1-a) are used as the citronellic acid derivative to run a Claisen condensation reaction between an optically active (R)-citronellic acid derivative and an undecenoate represented by the general formula (2), a (6R)-keto ester compound that is represented by the general formula (3-a) and maintains optical activity is produced.

The structure of the obtained optically active (6R)-keto ester compound represented by the general formula (3-a) can be confirmed by a nuclear magnetic resonance absorption spectroscopy, an infrared absorption spectroscopy or a high resolution mass spectroscopy. This (6R)-keto ester compound is an important intermediate in the production of an optically active muscone according to the present invention and is also a novel compound as will be explained later. Also, there has been no report as to the Claisen condensation reaction between the compounds, i.e., the optically active citronellic acid derivatives and undecenoate.

In the present invention, the obtained keto ester compound represented by the general formula (3) is hydrolyzed/decarboxylated to obtain 2,6-dimethyl-8-oxy-2,17-heptadecadiene represented by the formula (4). Specifically, the keto ester compound represented by the general formula (3) may be first hydrolyzed in a basic condition and then decarboxylated in an acidic condition. This reaction itself is well-known. Examples of the base used in the basic condition may include sodium hydroxide and potassium hydroxide and examples of the acid used in the acidic condition may include hydrochloric acid, sulfuric acid and p-toluenesulfonic acid. The reaction may be run in an alcoholic solvent, for example, methanol, ethanol or water.

In the present invention, next, the obtained 2,6-dimethyl-8-oxy-2,17-heptadecadiene represented by the formula (4) is subjected to a cyclization reaction run in the presence of a metathesis catalyst, specifically, to carry out ring closure metathesis, to obtain a 6-dehydromuscone represented by the formula (5). Examples of the metathesis catalyst used in this case may include a ruthenium catalyst and preferably benzylidenebis-(tricyclohexylphosphine)dichlororuthenium (first generation of Grubbs' catalyst) and 1,3-(bis(mesityl)-2-imidazolidinilidene) dichloro-(phenylmethylene)(tricyclohexylphosphine)ruthenium (second generation of Grubbs' catalyst).

The above cyclization reaction may be run in various solvents, for example, halide solvents such as dichloroethane, dichloromethane and chlorobenzene and hydrocarbon type solvents such as toluene and hexane, which do not particularly affect the reaction. There is no particular limitation as to the amount of the metathesis catalyst to be used. The wavy line in the formula shows that the obtained 6-dehydromuscone contains a sixth-position double-bond cis-isomer, a trans-isomer and a mixture of both.

In the present invention, finally the double bond at the sixth position of the obtained 6-dehydromuscone represented by the formula (5) is hydrogenated to obtain an intended muscone represented by the formula (6). The hydrogenating reaction of the double bond is well-known and no particular limitation is imposed on the hydrogenating method insofar as the double bond can be hydrogenated without any side reaction. Specifically, examples of the method include a method in which the 6-dehydromuscone is dissolved in various solvents which do not affect the reaction including ester type solvents such as ethyl acetate and butyl acetate, hydrocarbon type solvents such as toluene and hexane, alcohol type solvents such as methanol and ethanol and ether type solvents such as diethyl ether and tetrahydrofuran (THF) to hydrogenate it in the presence of a palladium-carbon catalyst under a hydrogen atmosphere.

The structure of the obtained muscone can be confirmed by a nuclear magnetic resonance absorption spectrum, an infrared absorption spectrum or a high resolution mass spectrum.

When, on the other hand, a (6R)-keto ester compound represented by the general formula (3-a) is used as the keto ester compound represented by the general formula (3) to carry out hydrolysis/decarbonization, a cyclization reaction using a metathesis catalyst and hydrogenation of the double bond, a (R)-muscone that is represented by the general formula (6-a) and maintains optical activity can be obtained.

The structure of the obtained (R)-muscone can also be confirmed by a nuclear magnetic resonance absorption spectrum, an infrared absorption spectrum or a high resolution mass spectrum.

EXAMPLES

The following examples involve the following steps. The number of a compound in the following reaction formula is identified in the following reaction formula.

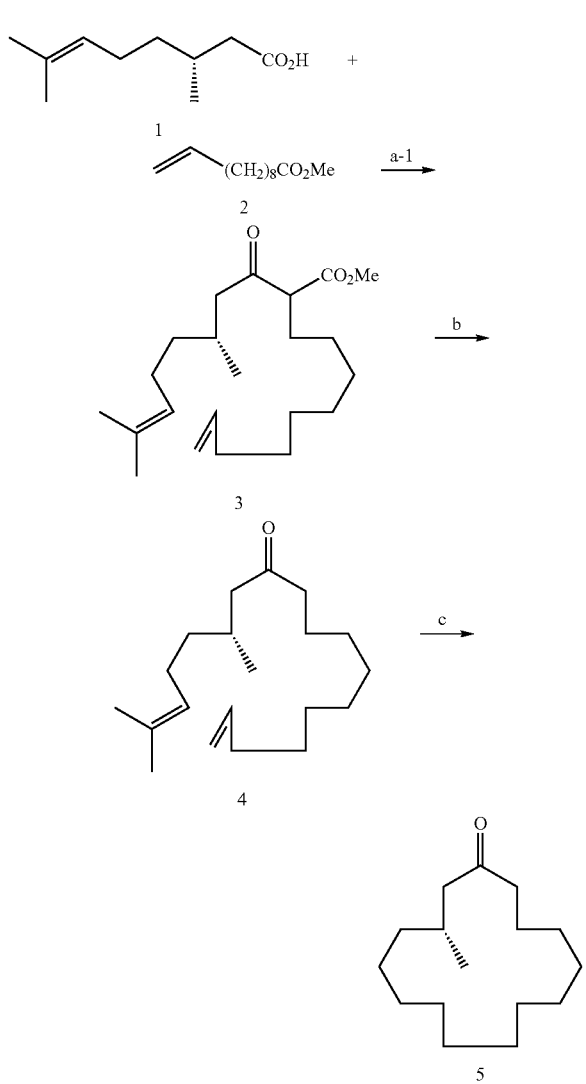

All reactions in the examples were run in a glass container dried in a drying furnace under an argon atmosphere. The instruments used in instrumental analyses are as follows.

NMR spectrum: JEOL DELTA 300

IR spectrum: JASCO FT/IR-5300

Mass analysis spectrum: JEOL JMS-T100LC

Production (Step a-1) of methyl (5R)-5,9-dimethyl-2-(8-nonenyl)-3-oxo-8-docecanoate (3) {(6R)-keto ester represented by the general formula (3-a) wherein R=methyl group}

170 mg (1.00 mmol) of (R)-citronellic acid derivative (1), 198 mg (1.20 mmol) of methyl 10-undecenoate (2) and 218 mg (1.2.0 mmol) of trichloroacetyl chloride $CCl_3COCl$ were dissolved in 2.0 ml of dichloromethane. This solution was added to a solution prepared by suspending 48 mg (1.20 mmol, purity: 60%) of sodium halide in 2.0 ml of dichloromethane, at 0 to 5° C. with stirring under an argon atmosphere, and the mixture was further stirred at the same temperature for 15 minutes. After the mixture was cooled to −45° C., a solution prepared by suspending 115 mg (1.20 mmol) of 1,2-dimethylimidazole in 0.2 ml of dichloromethane was added to the mixture, which was then stirred at the same temperature for 10 minutes. 385 μl (3.5 mmol) of titanium chloride (IV) $TiCl_4$ and 741 mg (4.00 mmol) of tributylamine were added to the resulting mixture, which was then stirred at the same temperature for 30 minutes. The reaction was suspended by adding 5 ml of water and the reaction solution was extracted with an ether twice. The organic phases were combined, washed with water and saturated brine in this order, dried by sodium sulfate and then concentrated. The resulting crude oily material was refined by silica gel column chromatography (hexane:ethyl acetate=75:1) to obtain 246 mg (yield: 75%) of the target compound.

The results of instrumental analysis were as follows.

Qualities: Colorless oily material (diastereomer mixture)

$^1$H NMR (300 MHz, $CDCl_3$) δ 0.88 (d, 3H×½, J=6.9 Hz), 0.89 (d, 3H×½, J=6.9 Hz), 1.10-1.44 (m, 12H), 1.59 (s, 3H), 1.68 (s, 3H), 1.73-2.08 (m, 7H), 2.23-2.57 (m, 2H), 3.41 (t, 1H×½, J=7.6 Hz), 3.42 (t, 1H×½, J=7.2 Hz), 3.71 (s, 3H), 4.87-5.03 (m, 2H), 5.03-5.13 (m, 1H), 5.80 (ddt, 1H, J=6.9, 10.3, 16.9 Hz)

$^{13}$C NMR (75 MHz, $CDCl_3$) δ 17.63, 19.52, 19.62, 25.39, 25.43, 25.68, 27.44, 28.09, 28.18, 28.36, 28.81, 28.95, 29.12, 29.27, 33.73, 36.67, 36.75, 49.20, 52.22, 59.33, 59.43, 114.15, 124.21, 131.51, 139.09, 170.33, 204.90, 205.04

IR (neat) 2928, 2857, 1748, 1717, 1437, 1200 cm$^{-1}$

HRMS (ESI) calcd for $C_{22}H_{38}O_3$ (M+Na$^+$) 373.2719, found 373.2719

Production (step b) of (R)-2,6-dimethyl-2,17-octadeca-dien-8-one (4)

1.0 ml of an aqueous 5 M sodium hydroxide solution was added to a solution prepared by dissolving 593 mg (1.69 mmol) of methyl (5R)-5,9-dimethyl-2-(8-nonenyl)-3-oxo-8-dodecanoate 3 in 3.0 ml of methanol at ambient temperature with stirring and further stirring the mixture at 70° C. for 20 minutes. The reaction solution was cooled to ambient temperature, 1.5 ml of 6 M aqueous hydrochloric acid was added to the reaction solution at the same temperature and the reaction solution was further stirred at 70° C. for 90 minutes. The mixture was extracted with an ether twice. The organic phases were washed with water and saturated brine in this order, dried by sodium sulfate and then concentrated. The resulting crude oily material was refined by silica gel column chromatography (hexane ethyl acetate=100:1) to obtain 468 mg (yield: 95%) of the target compound.

The results of instrumental analysis were as follows.

Qualities: Colorless oily material $^1$H NMR (300 MHz, $CDCl_3$) δ 0.89 (d, 3H, J=6.9 Hz), 1.10-1.44 (m, 12H), 1.46-1.62 (m, 2H), 1.60 (s, 3H), 1.68 (d, 3H, J=0.7 Hz), 1.88-2.09 (m, 5H), 2.20 (dd, 1H, J=7.9 Hz, Jgem=15.5 Hz), 2.32-2.43 (m, 3H), 4.87-5.03 (m, 2H), 5.03-5.13 (m, 1H), 5.81 (ddt, 1H, J=6.9, 10.3, 16.9 Hz)

$^{13}$C NMR (75 MHz, $CDCl_3$) δ 17.61, 19.75, 23.75, 25.45, 25.68, 28.87, 28.91, 29.04, 29.22, 29.27, 29.35, 33.77, 36.98, 43.35, 50.21, 114.10, 124.33, 131.42, 139.14, 211.33

IR (neat) 2926, 2855, 1715, 1460, 1375, 909 cm$^{-1}$

HRMS (ESI) calcd for $C_{20}H_{36}O$ (M+Na$^+$) 315.2664, found 315.2662

Production (step c) of (R)-3-methyl-1-cyclopentadecanone 5 {(R)-(−)-muscone}

A solution prepared by dissolving 10 mg (12 μmol) of ($H_2$IMes)($PCy_3$)$Cl_3$Ru=CHPh (second generation of a Grubbs catalyst) in 2.0 ml of dichloroethane was added to a solution prepared by dissolving 50 mg (0.17 mmol) of (R)-2,6-dimethyl-2,17-octadecadien-8-one 4 in 200 ml of dichloroethane, at 50° C. in an argon atmosphere and stirring the mixture at the same temperature for 11 hours. The reaction solution was concentrated under reduced pressure. 18 mg (17 μmol) of 10% palladium carbon was added to a solution obtained by diluting the concentrate with 2 ml of ethyl acetate. The mixture was stirred at ambient temperature for 9 hours while supplying hydrogen to the mixture from a hydrogen container. The mixture was subjected to filtration using celite in combination with a glass filter and the filtrate was concentrated under reduced pressure. The obtained crude oily material was purified by silica gel column chromatography (hexane:ethyl acetate=100:1) to obtain 30 mg (yield: 74%) of a target compound.

The results of instrumental analysis was as follows.

Qualities: Colorless oily material $^1$H NMR (300 MHz, $CDCl_3$) δ 0.94 (d, 3H, J=6.9 Hz), 1.16-1.41 (m, 20H), 1.51-1.75 (m, 2H), 1.97-2.11 (m, 1H), 2.18 (dd, 1H, J=5.2, 14.8 Hz), 2.36-2.47 (m, 3H)

$^{13}$C NMR (75 MHz, $CDCl_3$) δ 21.07, 23.00, 24.99, 26.12, 26.21, 26.48, 26.52, 26.56, 26.69, 27.07, 27.53, 29.02, 35.53, 42.05, 50.38, 212.09

IR (neat) 2930, 2861, 1713, 1460, 1368 cm$^{-1}$

Production (step a-2) of methyl (5R)-5,9-dimethyl-2-(8-nonenyl)-3-oxo-8-dodecanoate (3) (synthesis from (R)-citronellyl chloride (6))

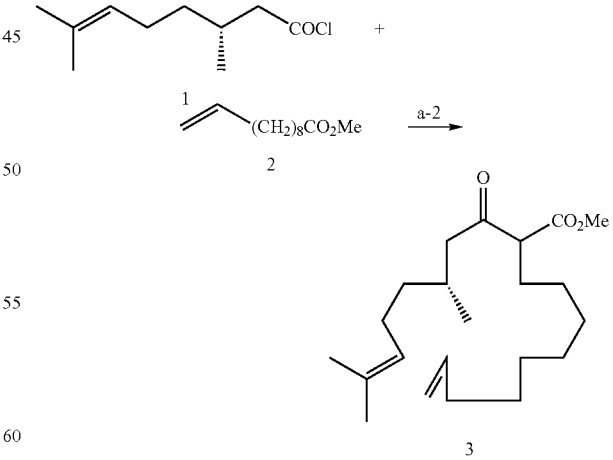

189 mg (1.00 mmol) of (R)-citronellyl chloride, 198 mg (1.2 mmol) of methyl 10-undecenoate and 115 mg (1.20 mmol) of 1,2-dimethylimidazole were dissolved in 2.0 ml of dichloromethane. The mixture was cooled to −45° C. and stirred at the same temperature for 10 minutes. 385 μl (3.50 mmol) of titanium chloride (IV) $TiCl_4$ and 741 mg (4.00 mmol) of tributylamine were added to the mixture, which was then stirred at the same temperature for 30 minutes. The reaction of the mixture was suspended by adding 5 ml of water and the reaction mixture was extracted twice with ether. The organic phases were washed with water and saturated brine in this order, dried by sodium sulfate and then concentrated. The resulting crude oily material was refined by silica gel column chromatography (hexane:ethyl acetate=75:1) to obtain 233 mg (yield: 66%) of the target compound and its structure was confirmed.

This application claims priority of Japanese patent application No. 2004-348409 filed Dec. 1, 2004, which is incorporated herein by reference.

What is claimed is:
1. A process for producing a muscone represented by the following formula (6):

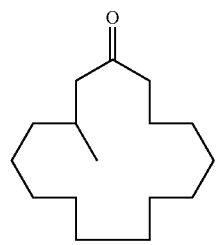

(6)

the process comprising:
(a) subjecting a citronellic acid derivative represented by the general formula (1):

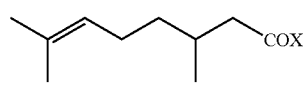

(1)

wherein X represents a hydroxyl group or a halogen atom, and an undecenoate represented by the following general formula (2):

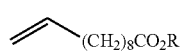

(2)

wherein R represents a lower alkyl group, to a Claisen condensation reaction, to produce a keto ester compound represented by the following general formula (3):

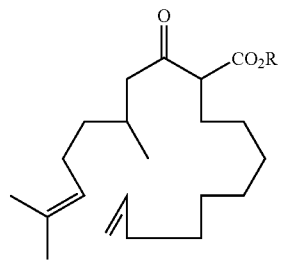

(3)

wherein R has the same meaning as above,
(b) decarboxylating the keto ester compound of formula (3) to produce 2,6-dimethyl-8-oxy-2,17-heptadecadiene represented by the following formula (4):

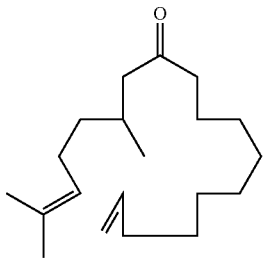

(4)

(c) cyclizing the heptadecadiene of formula (4) using a metathesis catalyst to produce a 6-dehydromuscone represented by the following formula (5)

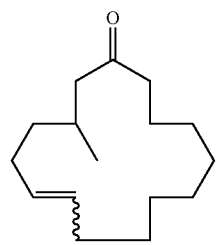

(5)

wherein the wavy line shows that a sixth-position double-bond cis-isomer and/or trans-isomer is contained, and
(d) hydrogenating the double bond of the 6-dehydromuscone of formula (5).

2. A process for producing a (R)-muscone represented by the following formula (6-a):

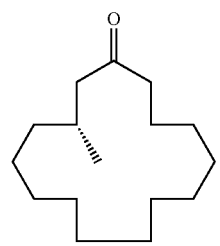

(6-a)

the process comprising:
(a) subjecting a (R)-citronellic acid derivative represented by the general formula (I-a):

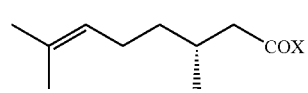

(1-a)

wherein X represents a hydroxyl group or a halogen atom, and an undecenoate represented by the following general formula (2):

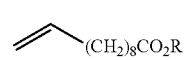

(2)

wherein R represents a lower alkyl group, to a Claisen condensation reaction, to produce a (6R)-keto ester compound represented by the following general formula (3-a):

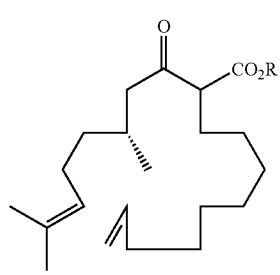

(3-a)

wherein R has the same meaning as above, (b) decarboxylating the keto ester compound of formula (3-a) to produce (6R)-2,6-dimethyl-8-oxy-2,17-heptadecadiene represented by the following formula (4-a):

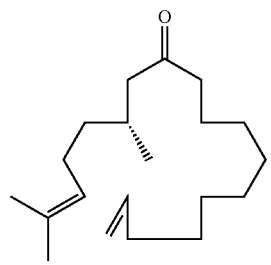

(4-a)

(c) cyclizing the heptadecadiene of formula (4-a) using a metathesis catalyst to produce a (R)-6-dehydromuscone represented by the following formula (5-a)

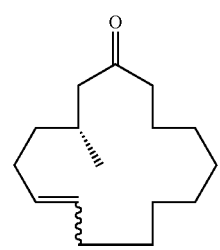

(5-a)

wherein the wavy line shows that a sixth-position double-bond cis-isomer and/or trans-isomer is contained, and (d) hydrogenating the double bond of the (R)-6-dehydromuscone of formula (5-a).

3. A process for producing a keto ester compound represented by the following general formula (3):

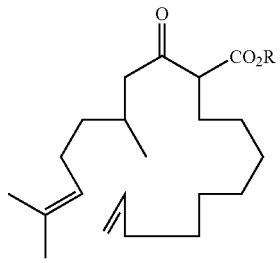

(3)

wherein R represents a lower alkyl group, the process comprising subjecting a citronellic acid derivative represented by the general formula (1):

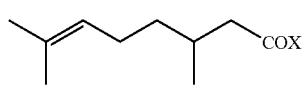

(1)

wherein X represents a hydroxyl group or a halogen atom, and an undecenoate represented by the following general formula (2):

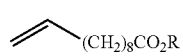

(2)

wherein R has the same meaning as above, to a Claisen condensation reaction.

4. A process for producing a (6R)-keto ester compound represented by the following general formula (3-a):

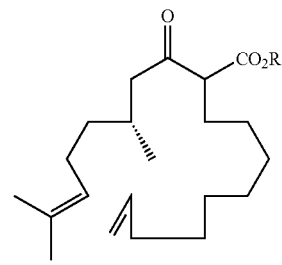

(3-a)

wherein R represents a lower alkyl group, the process comprising subjecting a (R)-citronellic acid derivative represented by the following general formula (1-a):

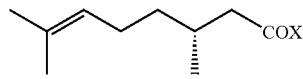

(1-a)

wherein X represents a hydroxyl group or a halogen atom, and an undecenoate represented by the following general formula (2):

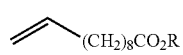

(2)

wherein R has the same meaning as above, to a Claisen condensation reaction.

5. A production process according to claim 1, wherein X in the general formula (1) representing the citronellic acid derivative is a hydroxyl group and the Claisen condensation reaction between the citronellic acid derivative represented by the general formula (1) and an undecenoate represented by the general formula (2) is carried out in the presence of a carboxylic acid activator, a titanium catalyst, a trialkylamine and an N-alkylimidazole.

6. A production process according to claim 2, wherein X in the general formula (1) representing the citronellic acid derivative is a hydroxyl group and the Claisen condensation reaction between the citronellic acid represented by the general formula (1) and an undecenoate represented by the general formula (2) is carried out in the presence of a carboxylic acid activator, a titanium catalyst, a trialkylamine and an N-alkylimidazole.

7. A production process according to claim 3, wherein X in the general formula (1) representing the citronellic acid derivative is a hydroxyl group and the Claisen condensation reaction between the citronellic acid represented by the general formula (1) and an undecenoate represented by the general formula (2) is carried out in the presence of a carboxylic acid activator, a titanium catalyst, a trialkylamine and an N-alkylimidazole.

8. A production process according to claim 4, wherein X in the general formula (1) representing the citronellic acid derivative is a hydroxyl group and the Claisen condensation reaction between the citronellic acid derivative represented by the general formula (1) and an undecenoate represented by the general formula (2) is carried out in the presence of a carboxylic acid activator, a titanium catalyst, a trialkylamine and an N-alkylimidazole.

9. A production process according to claim 1, wherein X in the general formula (1) representing the citronellic acid derivative is a halogen atom and the Claisen condensation reaction between the citronellic acid derivative represented by the general formula (1) and an undecenoate represented by the general formula (2) is carried out in the presence of a titanium catalyst, a trialkylamine and an N-alkylimidazole.

10. A production process according to claim 2, wherein X in the general formula (1) representing the citronellic acid derivative is a halogen atom and the Claisen condensation reaction between the citronellic acid derivative represented by the general formula (1) and an undecenoate represented by the general formula (2) is carried out in the presence of a titanium catalyst, a trialkylamine and an N-alkylimidazole.

11. A production process according to claim 3, wherein X in the general formula (1) representing the citronellic acid derivative is a halogen atom and the Claisen condensation reaction between the citronellic acid derivative represented by the general formula (1) and an undecenoate represented by the general formula (2) is carried out in the presence of a titanium catalyst, a trialkylamine and an N-alkylimidazole.

12. A production process according to claim 4, wherein X in the general formula (1) representing the citronellic acid derivative is a halogen atom and the Claisen condensation reaction between the citronellic acid derivative represented by the general formula (1) and an undecenoate represented by the general formula (2) is carried out in the presence of a titanium catalyst, a trialkylamine and an N-alkylimidazole.

13. A keto ester compound represented by the following general formula (3):

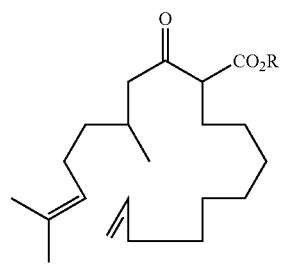

(3)

wherein R represents a lower alkyl group.

14. A (6R)-keto ester compound represented by the following general formula (3-a):

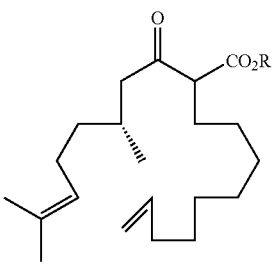

(3-a)

wherein R represents a lower alkyl group.

* * * * *